(12) United States Patent
Ciceron

(10) Patent No.: US 9,682,916 B2
(45) Date of Patent: Jun. 20, 2017

(54) MULTIFUNCTIONAL ACRYLATED ETHER-ESTER PRODUCTS, PROCESS FOR PREPARING SAME AND RELATED CROSSLINKABLE COMPOSITIONS

(71) Applicant: Arkema France, Colombes (FR)

(72) Inventor: Philippe Ciceron, Senlis (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/893,143

(22) PCT Filed: May 20, 2014

(86) PCT No.: PCT/FR2014/051174
§ 371 (c)(1),
(2) Date: Nov. 23, 2015

(87) PCT Pub. No.: WO2014/188117
PCT Pub. Date: Nov. 27, 2014

(65) Prior Publication Data
US 2016/0090349 A1     Mar. 31, 2016

(30) Foreign Application Priority Data
May 23, 2013  (FR) ..................................... 13 54651

(51) Int. Cl.
| | | |
|---|---|---|
| *C07C 69/54* | (2006.01) | |
| *C07C 67/31* | (2006.01) | |
| *C07C 69/73* | (2006.01) | |
| *C09D 4/00* | (2006.01) | |
| *C07C 67/08* | (2006.01) | |
| *C08F 220/20* | (2006.01) | |
| *C07C 69/734* | (2006.01) | |
| *C08F 222/20* | (2006.01) | |
| *C08F 222/10* | (2006.01) | |

(52) U.S. Cl.
CPC .............. *C07C 69/54* (2013.01); *C07C 67/08* (2013.01); *C07C 67/31* (2013.01); *C07C 69/734* (2013.01); *C08F 222/20* (2013.01); *C09D 4/00* (2013.01); *C08F 2222/104* (2013.01); *C08F 2222/108* (2013.01)

(58) Field of Classification Search
CPC ......... C07C 69/54; C07C 67/31; C07C 67/08; C07C 69/734; C09D 4/00; C08F 222/20; C08F 2222/104; C08F 2222/108
USPC ........................................................ 526/320
See application file for complete search history.

(56) References Cited

U.S. PATENT DOCUMENTS 5,243,069 A    9/1993  Emmons

FOREIGN PATENT DOCUMENTS

| JP | 2010 024380 | 2/2010 |
| JP | 2010024380 A | * 2/2010 |

* cited by examiner

*Primary Examiner* — Michael M Bernshteyn
(74) *Attorney, Agent, or Firm* — Christopher R. Lewis

(57) ABSTRACT

The present invention relates to novel multifunctional acrylic monomers which are acrylic ether-ester products based on a mixture of multifunctional acrylic products derived from the reaction of acrylic acid in deficit with a multifunctional polyol, to a preparation process for the same, and to crosslinkable compositions based on these products.

13 Claims, No Drawings

MULTIFUNCTIONAL ACRYLATED ETHER-ESTER PRODUCTS, PROCESS FOR PREPARING SAME AND RELATED CROSSLINKABLE COMPOSITIONS

CROSS-REFERENCE TO RELATED APPLICATIONS

This application is a national stage application under 35 U.S.C. §371 of PCT/FR2014/051174, filed May 20, 2014, which claims benefit to French patent application FR 13.54651, filed May 23, 2013.

The present invention relates to novel multifunctional acrylic monomers which are acrylic ether-ester products based on a mixture of multifunctional acrylic products derived from the reaction of acrylic acid in deficit with a multifunctional polyol, to a preparation process, to crosslinkable compositions based on these products, to finished products and to uses of the said acrylic products as multifunctional acrylic binders of high functionality for crosslinkable compositions of high crosslinking density and low shrinkage and more particularly for pigmented or non-pigmented coating compositions, in particular paints, varnishes, inks, adhesives or moulding or sealing compositions or composite compositions or chemical sealing compositions.

Multifunctional acrylic monomers of high functionality, of at least 3 and possibly ranging up to 6, as acrylate groups already exist and are used in coating applications such as varnishes or inks for increasing the crosslinking density and the related performance qualities, of chemical resistance or hardness.

However, the existing acrylic multifunctional monomers lead to poor flexibility, in particular for coating applications, the said flexibility being defined here in terms of resistance to folding determined by the folding test on a conical support. Thus, the hardness/flexibility compromise is poor, as is the adhesion to substrates, for example in applications for coatings such as varnishes or inks. This is essentially caused by an excessively high degree of crosslinking (which may be expressed by a density of crosslinking nodes per unit of weight) and shrinkage related to the large number of reacted unsaturations. Moreover, these monomers are based on specific multifunctional polyols such as polyol diethers of lower functionality, for example ditrimethylolpropane (DiTMP) or dipentaerythritol (DiPE), these products being difficult to access and costing many times that of the starting polyols, for example for DiTMP relative to trimethylolpropane (TMP) or for DiPE relative to pentaerythritol (PE). A practical, simpler and less expensive solution is thus sought, thus using starting polyols such as TMP or PE, this solution simultaneously needing to solve the technical problems and drawbacks observed above with the existing products.

The possible recourse to alkoxylation of the said starting polyols, which would make it possible to reduce the crosslinking density of the products obtained, moreover brings about a loss of reactivity, which is unacceptable since the reactivity is one of the essential stipulated properties, if not the essential property of these monomers.

The solution of the present invention overcomes these drawbacks with novel acrylic products having high functionalities, without using sophisticated and expensive starting materials such as polyethers or dendrimer structures, but only starting with base polyols commonly used in chemistry and ensuring a crosslinking density for the final products obtained that is sufficient without being too high and with significantly lower shrinkage, with a markedly improved compromise between hardness and flexibility as defined above and markedly improved adhesion.

The solution of the present invention consists of an acrylic product which is a mixture of products comprising hyperbranched polyether-esters of controlled structure and composition starting from common polyols and acrylic acid with a high and perfectly controlled mean functionality of acrylates by superposition of successive esterification and etherification reactions by Michael addition. Hyperbranched structures of high functionality are present therein, which, by sufficient lengthening via etherification or by Michael addition, enable both high functionality and a sufficient crosslinking density without any particular shrinkage, or any adhesion problems or any hardness/flexibility compromise. The lengthening by etherification (by Michael addition) is controlled by the mole ratio of acrylic acid in deficit relative to the OH groups of the said polyol.

Among the advantages of this solution relative to the prior art, mention may be made of the following:

very good control of a polyether-ester acrylate (PEEA) hyperbranched structure of low viscosity, low hydrophilicity (virtually all the hydroxyl groups are consumed) and very high functionality while at the same time maintaining a moderate double bond density, this structure allows the production of photo-crosslinked films of high flexibility without losing hardness, these products have a viscosity very much lower than that obtained by simple polyesterification (addition of a diacid) or by polyetherification by simple dehydration, another particular and important advantage is their very simple and very practical synthesis which requires only a single step, starting from a reactive mixture of a common polyol or a mixture of common polyols with acrylic acid in stoichiometric deficit, as sole reactants and with acidic catalysis and heteroazeotropic reflux to extract the esterification water and without any need for separation/purification of the final product. In contrast with common products, the product is not washed, but is neutralized, resulting in a better carbon imprint by reduction of the effluents (yield limited solely by the loss of esterification water), the final hydroxyl number is very low, resulting in low hydrophilicity relative to the water tolerance, or high hydrophobicity, which minimizes the environmental impact.

Among the other advantages of the solution according to the present invention, mention may be made in particular of the fact that the product according to the invention is a mixture of products of well-controlled and reproducible structure and composition, obtained in a single step, which may be used directly as such for the final application, without requiring expensive operations for the separation of by-products. The particular advantage of this final product is the fact that it has a molecular distribution with controlled presence of the starting acrylic monomer, which acts as reactive diluent for the application composition. Consequently, the final product generally does not require the addition of supplementary reactive diluent to adjust its viscosity. On the other hand, it is possible to use such a supplementary reactive diluent for the highest average molecular masses of the final product, as a function of the final application and of the required application viscosity. A particular advantage of the said products of the invention is their low volume shrinkage despite their high acrylate functionality.

The invention relates firstly to an acrylic product, which is in fact a multifunctional acrylic monomer or oligomer, which is the product of reaction of acrylic acid in deficit with a multifunctional polyol with production of a mixture of acrylic multifunctional monomers and oligomers, by simultaneous esterification and etherification reactions via Michael addition on the acrylate double bond of the excess hydroxyl groups borne by the acrylic esters obtained.

The second subject of the invention relates to a process for obtaining the said acrylic product as a mixture of multifunctional acrylic monomers and oligomers.

Another subject covered by the present invention relates to a crosslinkable composition comprising at least one acrylic product as defined according to the present invention.

Next, the invention also covers the use of the said acrylic products as a mixture or composition of multifunctional acrylic monomers/oligomers in crosslinkable compositions with a high crosslinking density and low shrinkage, in particular for pigmented or non-pigmented coating compositions, in particular paints, varnishes, index, adhesives or moulding or sealing compositions or composite compositions or chemical sealing compositions.

Finally, the invention covers finished products obtained by using an acrylic product according to the invention or by crosslinking of a crosslinkable composition of the invention (comprising the said acrylic product), said products being selected from: pigmented or non-pigmented coatings, in particular paints, varnishes, index, adhesives or moulding or sealing compositions or composite compositions or chemical sealing compositions.

Thus, the first subject of the present invention relates to a multifunctional acrylic product, in particular a mixture or composition of acrylic multifunctional monomers and oligomers, which product has a mean functionality of acrylate groups per mole of the said product of greater than 3, preferably between 3 and 14 and more preferentially from 4 to 14 and a density of the said groups ranging from 4 to 12 mmol per g of the said product, which acrylic product is the product of reaction by esterification and etherification, via Michael addition reaction, between at least one polyol $R(OH)_m$ with a functionality m of at least 3, preferably from 3 to 6 and more preferentially from 4 to 6, and acrylic acid ($R_1OH$), with the carboxyl groups of acrylic acid being in deficit relative to the hydroxyl groups of the said polyol, and which final product comprises in its final product composition at least the three defined acrylates according to the general formula (I) below and corresponding to:

n=0, n=1 and n=2 (mandatory presence of at least these three acrylic products in the said acrylic product):

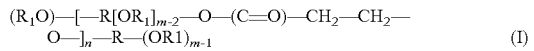

$$(R_1O)—[—R[OR_1]_{m-2}—O—(C=O)—CH_2—CH_2—O—]_n—R—(OR1)_{m-1} \quad (I)$$

with $R_1$ being the acryloyl radical (—(C=O)—CH=CH$_2$), R being the residual radical of the said polyol $R(OH)_m$ and n is the number of ether-ester repeating units obtained by Michael addition of the residual OH groups of the hydroxylated acrylate esters formed by partial esterification of the said polyol (by Michael addition) on the acrylate groups of the said acrylate esters.

According to a more particular option of the invention, the said product also comprises an acrylate of general formula (I) corresponding to n=3. This means that at least four acrylate products of indicated formula and with n indicated are present in the composition of the said product, which product is the mixture of monomers and oligomers having the formula according to (I). Even more particularly, the said product also comprises an acrylate of general formula (I) corresponding to n=4, which means that at least one of the acrylate products of indicated formula (I), monomers and oligomers corresponding to n=0 and n=1 and n=2 and n=3 and n=4 are present. In the present invention, "monomers" will be considered as the products with n=0 and 1 and "oligomers" will be considered as the products with n of at least 2.

As suitable polyols that may be used for the preparation of the said product defined according to the present invention, mention may be made of polyols or mixtures of polyols with a functionality of at least 3, preferably ranging from 3 to 6 and more preferentially from 4 to 6.

According to one variant, the product of the invention is a mixture of products of general formula (I) with a molecular distribution such that, for 80% by weight of the said distribution, n ranges from 0 to 4 and, for less than 20% of the said distribution, n is greater than 4, preferably with a corresponding number-average mass Mn ranging from 300 to 3000 and more preferentially from 300 to 2500 daltons. All the Mn values given herein below are in daltons.

According to a preferred option, the said product is obtained from a polyol with a functionality of at least 4 and it comprises linear products according to the general formula (I) and in addition at least one product of branched structure (or with a branched chain), preferably hyperbranched.

It should be noted that a branched structure according to the invention is a structure comprising at least one side graft on the main chain, the two, graft and main chain, being of the same nature. A hyperbranched structure according to the present invention is a structure containing per molecule at least 12 grafts of order 2 or of second generation, borne by grafts of order 1 or of first generation borne by the main chain.

More particularly, the product according to the invention may be obtained by simultaneous or successive and alternating esterification and etherification reactions between a mol of acrylic acid ($R_1OH$) and b mol of at least one polyol $R(OH)_m$ with a functionality m of at least 3 and preferably from 3 to 6, with an overall ratio r of equivalents r=a/(m*b) =CO$_2$H/OH ranging from a value greater than (m−1)/m and up to 0.95, preferably from 1.02*(m−1)/m to 0.95 and more preferentially from 1.035*(m−1)/m to 0.95. The said polyol may be selected from polyol monomers and/or polyol oligomers and, in the latter case (polyol oligomers), with a number-average mass Mn not exceeding 600 and preferably not exceeding 400. A polyol monomer that is suitable for the invention may be selected from: pentaerythritol (PET), trimethylolpropane (TMP), alkoxylated pentaerythritol, alkoxylated trimethylolpropane, alkoxylated glycerol, sorbitol, erythritol, xylitol, preferably pentaerythritol, trimethylolpropane, alkoxylated pentaerythritol, alkoxylated trimethylolpropane, sorbitol. Preferably, and when the said polyol is alkoxylated, there are from 1 to 4 alkoxy units. A suitable polyol oligomer may be selected from: polyether polyols, polyester polyols, hydroxylated acrylic oligomers. The hydroxylated acrylic oligomers may be, for example, oligomeric copolymers based on hydroxyalkyl (meth)acrylates, with the content of the said hydroxyalkyl (meth) acrylate setting the functionality of the said oligomer.

The said product of the invention may be obtained from a mixture of polyols as defined above. More particularly, in addition to the said polyol with a functionality of at least 3, there is a second polyol different from the first and with a functionality of at least 2. This option thus makes it possible to adjust the mean functionality f and the compatibility of the binder with the other components as a function of the final application.

The chain length of the said acrylic product according to the invention is characterized by the index n, which corresponds to the number of ether-ester units linked by successive Michael addition reactions of an OH of the said polyol to the acrylic acid, followed by the esterification of a residual OH (from m−1) of the said polyol with another acrylic acid molecule whose unsaturation can once again become the site of another Michael addition with an OH of another molecule of the said polyol. A mean index n may be estimated for a total conversion from the equivalent ratio $r=CO_2H/OH$ and the functionality m of the said polyol by the following relationship:

$$n=[(1-r)/(r-1+/m)]$$

Starting with an average n, it is possible to calculate a number-average molecular mass Mn given the molecular weight (mw) of the repeating units and formula I described above.

Similarly, an average functionality of acrylate groups per acrylic product can be estimated (calculated) from the average n described above, the functionality m of the said polyol and formula I. It should be noted that in the case of a mixture of two polyols of functionalities m1 and m2 at mole ratios x1 and x2 (x1+x2=1) respectively in the said mixture, in this case, the functionality m to be used is the number-average (molar) of the two polyols according to the following relationship:

$$m \text{ average}=x1*m1+x2*m2.$$

In the case of a mixture of several polyols i of functionality $m_i$ and of mole ratios $x_i$ ($\Sigma_i x_i=1$), the average functionality m will be equal to $m=\Sigma_i x_i*m_i$.

Preferably, n average may range from 0.3 to 12 and more preferentially from 0.35 to 10.

The second subject of the present invention relates to a process for preparing a product according to the invention as described above, which process comprises the following steps:
i) mixing in a reactor of acrylic acid and of the said polyol in proportions such that the overall equivalent ratio $r=CO_2H/OH$ is within a range having a value greater than m−1/m and up to 0.95, preferably from 1.02*(m−1)/m to 0.95 and more preferentially from 1.035*(m−1)/m to 0.95, in the presence of an acidic esterification catalyst and of a solvent forming an azeotrope with water, to form the reaction mixture, followed by
ii) refluxing the said reaction mixture, with simultaneous or successive and alternating esterification reactions, by reaction of acrylic acid with a hydroxyl of the said polyol, and etherification reactions, via Michael addition reaction of a hydroxyl of the said polyol to a formed acrylate group and gradual removal of the esterification water, with
iii) continuation of the reaction until all of the OH functions have been consumed by Michael addition, and
iv) neutralization of the said acidic catalyst for recovery of the said final product, by removal of the said solvent, without any other specific purification step required.

The solvent forming an azeotrope with water is selected in particular from heptane and toluene or a mixture of these solvents in a volume ratio ranging from 25/75 to 75/25. The weight ratio of the solvent in the reaction mixture ranges from 10% to 40%. The reflux range of step ii) is preferably from 95 to 130° C. and more preferentially from 100 to 120° C. Acidic esterification catalysts that may be used are acids such as methanesulfonic acid (MSA) or p-toluenesulfonic acid (PTSA), $H_2SO_4$ and preferably p-toluenesulfonic acid. Preferably, the catalyst content ranges from 1% to 10% and more preferentially from 2% to 5% by weight relative to the said polyol. The consumption of the OH groups (or functions) may be monitored by measuring the OH number of the finished product. Similarly, the consumption of the $CO_2H$ groups may be monitored by measuring the acid number of the said product. Preferably, in the final product, more than 95% of the starting OH groups are consumed or converted in the form of ester and ether. Preferably, the OH number corresponding to the final product is less than 6 mg KOH/g, like the acid number, which also remains below 6 mg KOH/g. Neutralization of the acidic catalyst is performed with a soluble organic neutralizing agent, for instance an amine such as a tertiary or secondary amine, or with a solid mineral neutralizing agent, for instance sodium carbonate, in the form of a neutralizing bed on which the reaction mixture can be filtered.

Attention should be paid in particular to the advantage of this process, which makes it possible, with a single reaction mixture (acrylic acid and polyol or mixture of polyols) and simple regulation of the ratio $r=CO_2/OH$, to have a multifunctional acrylic final product which has a well-defined and controlled molecular distribution, with use of the said product as obtained, without any need for separating out or purifying the final product, or even any constraining need for dilution and adjustment of the viscosity for the final application. This latter advantage is due to the presence of the monomer corresponding to n=0 in the said product, acting as an internal reactive diluent for the final application. This further demonstrates the advantages of the said process and of the present invention in general.

Another subject of the present invention concerns a crosslinkable composition which comprises at least one product as described above or obtained via a process as defined above according to the invention.

This composition may comprise, in addition to the said acrylic product of the invention, in particular in the case where the Mn is greater than 1000 and preferably greater than 1500, at least one reactive diluent selected from acrylic monomers, which are preferably multifunctional. The essential role of this diluent, if need be, is to adjust the viscosity as a function of the final application.

More particularly, the said composition is radiation-crosslinkable, in particular under UV in the presence of a photoinitiating system or via an electron beam (EB) and in the absence in this case of a photoinitiating system and/or via a thermal radical initiating system, in particular via a peroxide initiating system (P-cure) and/or via Michael addition (M-cure) or via a mixed system, in particular by dual crosslinking (dual cure) in which the two abovementioned systems are present.

The said crosslinkable composition is more particularly a pigmented or non-pigmented coating composition, preferably chosen from: paint, varnish, ink, adhesive and gel coat or a composition for 3D (three-dimensional) articles with successive layers or a moulding composition or a sealing composition or a composite composition or a chemical sealing composition.

The invention also covers the use of the said product as described above or obtained via a process as defined according to the invention in crosslinkable compositions, in particular having a low degree of shrinkage. More particularly, such a use applies to pigmented or non-pigmented coating compositions, in particular paints, varnishes, inks, adhesives and gel coats or compositions for 3D (three-dimensional) articles with successive layers or moulding or sealing compositions or composite compositions or chemical sealing compositions.

Finally, the invention also relates to the finished products obtained, which result from the use of at least one product as defined above or obtained via a process as defined above according to the invention or from the crosslinking of a crosslinkable composition as defined above according to the invention and preferably finished products chosen from pigmented or non-pigmented coatings, in particular chosen from paints, varnishes, inks, adhesives and gel coats or 3D (three-dimensional) articles with successive layers or moulded pieces or seals or composites or chemical seals.

The examples that follow are presented as illustrations of the invention and of its performance qualities, and do not in any way limit the scope of the invention.

EXAMPLES

1) Starting Materials Used (see Table 1)

TABLE 1 starting materials used

| Trade name (REF) | Chemical name | Abbreviated name | Supplier | Function according to the invention | Functionality |
|---|---|---|---|---|---|
| Penta radcure | Pentaerythritol | PET | Perstorp | Polyol | 4 |
| TMP (Hydro) flakes | Trimethylol propane | TMP | BASF | Polyol | 3 |
| Glacial acrylic acid | Acrylic acid | AA | Arkema | Acrylic acid | 1 |
| Toluene | Toluene | Tol | TOTAL | Solvent | |
| MSA E-pure | Methanesulfonic acid | MSA | Arkema | Catalyst | |
| Extra pure hydroquinone | Hydroquinone | HQ | Rhodia | Inhibiter | |
| para-Methoxy phenol flakes | Hydroquinone methyl ether | HQME | Rhodia | Inhibiter | |
| CN131B | Epoxyacrylate | O-1 | Sartomer | Acrylate oligomer | |
| Darocur ® 1173 | 2-Hydroxy-2-methyphenyl-propan-1-one | PI-1 | BASF | Photoinitiator | |
| Dipropylamine | Dipropylamine | | BASF | Neutralizing agent | |
| SR 399 | Dipentaerythrityl hexaacrylate | | Sartomer | Reference acrylic product vs prior art | 6 |

2) Preparation of the Products According to the Invention 2.1) Procedure for Examples According to the Invention (Examples 1 to 4)

The ratio r mentioned above in the examples corresponds to the $CO_2H/OH$ equivalent ratio r.

Example 1: PET with r=COOH/OH=0.93 (Invention)

450.35 g of acrylic acid (AA) (6.2263 mol), 228.36 g of pentaerythritol (PET) (1.6714 mol), 301.38 g of toluene, 13.83 g of methanesulfonic acid as a 70% aqueous solution (MSA-aq) (0.1004 mol), 4.50 g of hydroquinone (HQ) and 1.58 g of hydroquinone methyl ether (HQME) are introduced into a 1 liter reactor equipped with an anchor stirrer and on which is mounted a florentine tube with its condenser (device enabling continuous withdrawal of the esterification water under solvent reflux), an air inlet (air sparge) and a thermometer probe.

The reaction mixture is refluxed for 14 hours, thus passing from a temperature of 100° C. (start of boiling) to 117° C. at the time of stoppage of the esterification by cooling the reaction medium, after having distilled off 117.5 ml of water.

This organic phase is neutralized at 50° C. with 17.34 g of dipropylamine (0.1864 mol) and with stirring for 1 hour before distillation under vacuum at 80-95° C. and 200-100 millibar until the solvent has been completely removed (with residual toluene<0.1%).

A poly(ether-ester) polyacrylate product A-1 having the following characteristics is obtained:
Appearance: clear
Turbidity: 4%
Viscosity at 25° C.: 7.4 Pa·s
Residual acidity or acid number of the product: 4.6 mg KOH/g
OH number of the product: 0.73 mg KOH/g A formulation F-1 having the following percentage composition is prepared by simple cold mixing:
A-1: 20%
O-1: 76%
PI-1: 4%

Characteristics of the Formulation F-1;
Reactivity: 15 m/min
Persoz hardness: 77 s
Flexibility: 4 mm
Resistance to acetone: >300 s Example 2: PET but with r=0.85 (Invention)

467.45 g of acrylic acid (AA) (6.4924 mol), 259.34 g of pentaerythritol (PET) (1.9069 mol), 251.19 g of toluene, 15.71 g of methanesulfonic acid as a 70% aqueous solution (MSA-aq) (0.1145 mol), 4.67 g of hydroquinone (HQ), 1.64 g of hydroquinone methyl ether (HQME).

The reaction mixture is refluxed for 19 hours, thus passing from a temperature of 100° C. (start of boiling) to 120° C. at the time of stoppage of the esterification by cooling the reaction medium, after having distilled off 122 ml of water. The neutralization of the organic phase and the removal (distillation) of the solvent and recovery of the finished product is similar to that described for Example 1.

A poly(ether-ester) polyacrylate product A-2 having the following characteristics is obtained:
Appearance: clear
Turbidity: 5.5%
Viscosity at 25° C.: 72 Pa·s
Residual acidity (acid number): 1.3 mg KOH/g
OH number of the product: <5

Example 3: TMP with r=0.75 (Invention)

372.02 g of acrylic acid (AA) (5.1669 mol), 307.65 g of trimethylolpropane (TMP) (2.2959 mol), 301.14 g of toluene, 14.17 g of methanesulfonic acid as a 70% aqueous solution (MSA-aq) (0.1033 mol), 3.72 g of hydroquinone (HQ), 1.30 g of hydroquinone methyl ether (HQME).

The reaction mixture is refluxed for 13 hours, thus passing from a temperature of 100° C. (start of boiling) to 120° C. at the time of stoppage of the esterification by cooling the reaction medium, after having distilled off 98 ml of water. The neutralization of the organic phase and the removal (distillation) of the solvent and recovery of the finished product is similar to that described for Example 1.

A poly(ether-ester) polyacrylate product A-3 having the following characteristics is obtained:
Appearance: clear
Turbidity: 4.2%
Viscosity at 25° C.: 8.2 Pa·s
Residual acidity (acid number): 3.3 mg KOH/g
OH number of the product: <5

Example 4: TMP with r=0.70 (Invention)

360.19 g of acrylic acid (AA) (5.0026 mol), 319.15 g of trimethylolpropane (TMP) (2.3817 mol), 301.11 g of toluene, 14.70 g of methanesulfonic acid as a 70% aqueous solution (MSA-aq) (0.1072 mol), 3.60 g of hydroquinone (HQ), 1.26 g of hydroquinone methyl ether (HQME).

The reaction mixture is refluxed for 15 hours, thus passing from a temperature of 100° C. (start of boiling) to 119° C. at the time of stoppage of the esterification by cooling the reaction medium, after having distilled off 97.5 ml of water. The neutralization of the organic phase and the removal (distillation) of the solvent and recovery of the finished product is similar to that described for Example 1.

A poly(ether-ester) polyacrylate product A-4 having the following characteristics is obtained:
Appearance: clear
Turbidity: 4.6%
Viscosity at 25° C.: 68 Pa·s
Residual acidity (acid number): 3.2 mg KOH/g
OH number of the product: <5

Example 5: PET+TMP Mixture, r=0.92 (Invention)

462.15 g of acrylic acid (AA) (6.4188 mol), 189.69 g of pentaerythritol (PET) (1.3948 mol), 62.30 g of TMP (0.4649 mol), 264.36 g of toluene, 15.25 g of methanesulfonic acid as a 70% aqueous solution (MSA-aq) (0.1112 mol), 4.62 g of hydroquinone (HQ), 1.62 g of hydroquinone methyl ether (HQME).

The reaction mixture is refluxed for 20 hours, thus passing from a temperature of 100° C. (start of boiling) to 120° C. at the time of stoppage of the esterification by cooling the reaction medium, after having distilled off 80 ml of water. The neutralization of the organic phase and the removal (distillation) of the solvent and recovery of the finished product is similar to that described for Example 1.

A poly(ether-ester) polyacrylate product A-5 having the following characteristics is obtained:
Appearance: clear
Turbidity: 8.7%
Viscosity at 25° C.: 2.6 Pa·s
Residual acidity (acid number): 5.1 mg KOH/g
OH number of the product: <5

Example 6: PET+TMP Mixture, r=0.75 (Invention)

382.69 g of acrylic acid (AA) (5.3152 mol), 74.04 g of pentaerythritol (PET) (0.5444 mol), 219.7 g of TMP (1.6356 mol), 301.17 g of toluene, 17.76 g of methanesulfonic acid as a 70% aqueous solution (MSA-aq) (0.1295 mol), 3.83 g of hydroquinone (HQ), 1.34 g of hydroquinone methyl ether (HQME).

The reaction mixture is refluxed for 11 hours, thus passing from a temperature of 100° C. (start of boiling) to 118° C. at the time of stoppage of the esterification by cooling the reaction medium, after having distilled off 73 ml of water. The neutralization of the organic phase and the removal (distillation) of the solvent and recovery of the finished product is similar to that described for Example 1.

A poly(ether-ester) polyacrylate product A-6 having the following characteristics is obtained:
Appearance: clear
Turbidity: 11.7%
Viscosity at 25° C.: 48 Pa·s
Residual acidity (acid number): 1.26 mg KOH/g
OH number of the product: <5

It is found in all these examples that the water removed (distilled off) corresponds to virtually complete esterification of the carboxyl groups of AA.

The molecular characteristics of the products obtained are presented below in Table 2.

TABLE 2

Molecular characteristics of the products prepared according to the invention

| Example REF | Polyol | Functionality Polyol (or average vs mixture) | r = $CO_2$/OH | Calc. average n | Calc. Mn (g/mol) | Mn GPC | Calc. average number of acrylates per chain | Calc. acrylates mmol/g |
|---|---|---|---|---|---|---|---|---|
| A-1 | PET | 4 | 0.93 | 0.39 | 468 | 740 | 4.78 | 10.21 |
| A-2 | PET | 4 | 0.85 | 1.5 | 799 | | 7.00 | 8.76 |
| A-3 | TMP | 3 | 0.75 | 3.0 | 1022 | | 6.00 | 5.87 |
| A-4 | TMP | 3 | 0.70 | 9.0 | 2474 | | 12.00 | 4.85 |
| A-5 | PT/TMP | 3.75 | 0.93 | 0.43 | 460 | | 4.50 | 9.79 |
| A-6 | PT/TMP | 3.25 | 0.75 | 4.33 | 1271 | | 8.67 | 6.82 |

TABLE 3

| | weight % distribution according to n (by liquid chromatography HPLC) | | | | | |
|---|---|---|---|---|---|---|
| Example REF | n = 0 | n = 1 | n = 2 | n = 3 | n = 4 | n > 4 |
| A-1 | 44% | 14% | 8% | 8% | 6% | 20% |

Measurement and Characterization Methods

Determination of the Appearance:

The product is observed visually in daylight, through a 60 ml colourless glass bottle, to determine whether the product is:

Clear: no turbidity, it is comparable to water,
Hazy: not allowing a clear view through the bottle,
Cloudy: opaque bottle, no image can be seen through the bottle.

Determination of the Turbidity:

This is the percentage of scattered light relative to the total light transmitted by the sample contained in a 50 ml transparent tank (60 mm×40 mm×20 mm). The measurement is taken using a Hunterlab "Colorquest XE"® spectrocolorimeter.

Determination of the Noury Viscosity:

The time of travel, in the liquid to be characterized, of a steel ball under its own gravity is measured. Standard AFNOR XP.T51-213 in particular specifies the geometry of the container, the diameter of the ball (2 mm) and the path of the ball (104 mm). Under these conditions, the dynamic viscosity is proportional to the time of travel of the ball with: 1 second $\Leftrightarrow$ 0.1 Pa·s.

Determination of the Residual Acidity:

The acidity of the product to be characterized is expressed in milligrams of potassium equivalent per gram of product. To do this, an acid-base titration is performed under the following conditions: a mass m of product (approximately exactly 10 g) is dissolved in 50 ml of a toluene/ethanol mixture (2 vol/1 vol). After total dissolution, titration is performed with a potassium hydroxide solution of normality N (approximately exactly 0.1 N). The equivalent point is detected by a combined electrode controlling an automatic burette (Metrohm "716 DMS Titrino"® automatic titration machine) delivering the equivalent volume $V_E$. After performing a blank test (50 ml of the toluene/ethanol mixture alone), which allows the equivalent volume $V_B$ to be determined, the acid number (IA) is calculated via the formula $IA=(V_E-V_B)*N*56.1/m$.

Determination of the Reactivity:

The formulation F### is applied as a 12 μm film on a contrast card (Leneta "Penoparc charts form 1B"®), and is then crosslinked using a 120 W/cm Hg Fusion lamp. The minimum passage rate (in m/min) necessary to obtain a touch-dry film is measured.

For the following hardness, flexibility and acetone resistance tests, the photo-crosslinked films are left in an air-conditioned room (T=23° C.) for 24 hours after crosslinking and before the measurements.

Determination of the Persoz Hardness:

The formulation to be examined is applied as a 100 μm film on a glass plate and crosslinked with a 120 W/cm Hg Fusion lamp at a rate of 8 m/min.
The number of oscillations before damping of the oscillations (passing from 12° to 4° of amplitude) of a pendulum in contact with the coated glass plate is measured according to standard ISO 1522.

Determination of the Flexibility:

The formulation F### is applied as a 100 μm film to a 25/10 mm thick smooth steel plate (D-46® Q-Panel) and then crosslinked with a 120 W/cm Hg Fusion lamp at a rate of 8 m/min.
The coated plate is curved on cylindrical mandrels according to standard ISO 1519. The result is expressed as the value (in mm) of the smallest radius of curvature that can be imposed on the coating without it cracking or becoming detached from the support.

Determination of the Acetone Resistance:

The formulation F### is applied as a 12 μm film to a glass plate, and then crosslinked with a 120 W/cm Hg Fusion lamp at a rate of 8 m/min.
The coating is rubbed with a cloth soaked with acetone. The result is the time (expressed in seconds) beyond which the film becomes detached and/or disintegrates.

Number-Average Molecular Mass Mn:

Calculated according to the method stated in the description and/or measured by GPC in THF as solvent and Mn is expressed as polystyrene equivalents on columns calibrating with polystyrene standards.

Acrylates Per Unit of Weight Calculated from the Material Balance and/or Measured by $^{13}C$ NMR:

Weight distribution (%) of n: by HPLC with a diode array UV detector (230 nm).

Water Tolerance:

Direct measurement of the limit amount of water beyond which the water-product mixture becomes cloudy by demixing (at room temperature) is relatively imprecise. This is why recourse was made to an indirect method: the cloud point (water-product demixing temperature) was measured for two known compositions (approximately exactly 2% and 4% of water, for example); the limit demixing composition was then determined by linear interpolation of this value at room temperature (20° C.).

Shrinkage:

This is measured via the radius of curvature of a crosslinked standard film (after crosslinking) with three different levels of curvature caused by shrinkage (shrinkage creates internal tensions in the film which make it curve) with the radius of curvature inversely increasing with the shrinkage:
1) zero radius (0: best result)
2) radius between 10 and 20 cm
3) radius<5 cm Evaluation Results:

These results are presented in Table 4 below on formulations.

TABLE 4 results of the performance of the coating compositions
All the formulations tested are identical to the
composition of formulation F-1 described on page 10.

| Test PERFORMANCE | REF of the acrylic product in the formulation tested | | | | | | |
|---|---|---|---|---|---|---|---|
| | A-1 | A-2 | A-3 | A-4 | A-5 | A-6 | SR 399 |
| Reactivity (m/min) | 15 | 15 | 10 | 10 | 10 | <5 | 25 |
| Persoz hardness | 77 | 68 | 46 | 50 | 94 | 54 | 135 |
| Flexibility | 4 | <3 | <3 | <3 | 4 | >3 | 10 |
| Acetone resistance (s) | >300 | >300 | 65 | 60 | >300 | 205 | >300 |
| Shrinkage Curvature (cm) | 10-20 | 10-20 | 0 | 0 | 10-20 | 0 | <5 |
| Tolerance vs water (%) | 0.6 | | | | | | 1.25 |

All the formulations tested are identical to F-1 described on page 10, except for the shrinkage measurement, in which formulation F-2 below is used:
Acrylic product according to the invention (A-1 to A-6) and reference product: 96%
PI-1:4%

The invention claimed is:
1. A multifunctional acrylic product having a mean functionality of acrylate groups per mole of product greater than 3 and a density of groups from 4 to 12 mmol per g of said product, produced by esterification and etherification, via Michael addition reaction, between at least one polyol $R(OH)_m$ with a functionality m of at least 3, and acrylic acid ($R_1OH$), with a ratio of carboxyl groups of acrylic acid to hydroxyl groups of said polyol having a value of from ⅔ to 0.95, and which final product comprises at least three acrylates according to formula (I) and corresponding to n=0, n=1, and n=2:

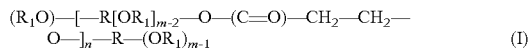
(I)

with $R_1$ being the acryloyl radical (—(C=O)—CH=CH$_2$), R being the residual radical of said polyol $R(OH)_m$ and n is the number of ether-ester repeating units obtained by Michael addition of residual OH groups of hydroxylated acrylate esters formed by partial esterification of said polyol by Michael addition on the acrylate groups of said acrylate esters.

2. A composition comprising a mixture of multifunctional acrylic products, wherein each of said multifunctional products has a mean functionality of acrylate groups per mole of product greater than 3 and a density of groups from 4 to 12 mmol per g of said product, produced by esterification and etherification, via Michael addition reaction, between at least one polyol $R(OH)_m$ with a functionality m of at least 3, and acrylic acid ($R_1OH$), with a ratio of carboxyl groups of acrylic acid to hydroxyl groups of said polyol having a value of from ⅔ to 0.95, and which final product comprises at least three acrylates according to formula (I) and corresponding to n equals at least 0:

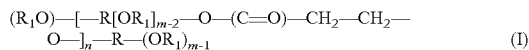
(I)

with $R_1$ being the acryloyl radical (—(C=O)—CH=CH$_2$), R being the residual radical of said polyol $R(OH)_m$ and n is the number of ether-ester repeating units obtained by Michael addition of residual OH groups of hydroxylated acrylate esters formed by partial esterification of said polyol by Michael addition on the acrylate groups of said acrylate esters, wherein for at least 80% by weight of the products, wherein n of formula (I) is from 0 to 4, and, for less than 20% of the products, wherein n is greater than 4 with a corresponding number-average mass Mn ranging from 300 to 3000.

3. A product according to claim 1 wherein said polyol has a functionality m of at least 4 and wherein said product comprises linear products according to the formula (I) and at least one product of branched structure.

4. A product according to claim 1 obtained by simultaneous or successive and alternating esterification and etherification reactions.

5. A product according to claim 1 wherein, said polyol is selected from the group consisting of polyol monomers and polyol oligomers with an Mn (polyol oligomers) not exceeding 600.

6. A product according to claim 5, wherein said polyol is a polyol monomer selected from the group consisting of pentaerythritol, trimethylolpropane, alkoxylated pentaerythritol, alkoxylated trimethylolpropane, alkoxylated glycerol, sorbitol, erythritol, xylitol, preferably pentaerythritol, trimethylolpropane, alkoxylated pentaerythritol, alkoxylated trimethylolpropane, and sorbitol.

7. A product according to claim 5, wherein said polyol is a polyol oligomer selected from the group consisting of polyether polyols, polyesterpolyols and hydroxylated acrylic oligomers.

8. A product according to claim 1 wherein in addition to said polyol with a functionality of at least 3, there is a second polyol different from the first with a functionality of at least 2.

9. A process for preparing a product according to claim 1 comprising the steps:
   i) forming a reaction mixture by mixing in a reactor of acrylic acid and said polyol in proportions such that the overall equivalent ratio $r=CO_2H/OH$ is within a range having a value of from ⅔ to 0.95, in the presence of an acidic esterification catalyst and a solvent forming an azeotrope with water, followed by
   ii) refluxing said reaction mixture, with simultaneous or successive and alternating esterification reactions, by of reacting acrylic acid with hydroxyl of said polyol, and etherification reactions, via Michael addition reaction of hydroxyl of said polyol to a formed acrylate group and gradual removal of the esterification water,
   iii) continuing the reaction until all of the OH functions have been consumed by Michael addition, and
   iv) neutralizing said acidic catalyst for recovery of said final product, by removal of the said solvent.

10. A composition comprising at least one product according to claim 1, wherein the composition is a radiation-crosslinkable and/or crosslinkable via a thermal radical initiating system and/or crosslinkable via Michael addition (M-cure) or a mixed system.

11. A composition according to claim 10 wherein for Mn greater than 1000, the composition also comprises at least one reactive diluent selected from the group consisting of acrylic monomers.

12. A multifunctional acrylic product having a mean functionality of acrylate groups per mole of product greater than 3 and a density of groups from 4 to 12 mmol per g of said product, produced by esterification and etherification, via Michael addition reaction, between at least one polyol $R(OH)_m$ with a functionality m of at least 3, and acrylic acid ($R_1OH$), with a ratio of carboxyl groups of acrylic acid to hydroxyl groups of said polyol having a value of from ⅔ to 0.95, and which final product comprises four acrylates according to formula (I) and corresponding to n=0, n=1, n=2, and n=3:

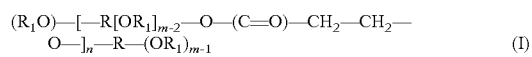
(I)

with $R_1$ being the acryloyl radical (—(C=O)—CH=CH$_2$), R being the residual radical of said polyol $R(OH)_m$ and n is the number of ether-ester repeating units obtained by Michael addition of residual OH groups of hydroxylated acrylate esters formed by partial esterification of said polyol by Michael addition on the acrylate groups of said acrylate esters.

13. A multifunctional acrylic product having a mean functionality of acrylate groups per mole of product greater than 3 and a density of groups from 4 to 12 mmol per g of said product, produced by esterification and etherification, via Michael addition reaction, between at least one polyol $R(OH)_m$ with a functionality m of at least 3, and acrylic acid ($R_1$OH), with a ratio of carboxyl groups of acrylic acid to hydroxyl groups of said polyol having a value of from ⅔ to 0.95, and which final product comprises five acrylates according to formula (I) and corresponding to n=0, n=1, n=2, n=3, and n=4:

$$(R_1O)-[-R[OR_1]_{m-2}-O-(C=O)-CH_2-CH_2-O-]_n-R-(OR_1)_{m-1} \quad (I)$$

with $R_1$ being the acryloyl radical ($-(C=O)-CH=CH_2$), R being the residual radical of said polyol $R(OH)_m$ and n is the number of ether-ester repeating units obtained by Michael addition of residual OH groups of hydroxylated acrylate esters formed by partial esterification of said polyol by Michael addition on the acrylate groups of said acrylate esters.

* * * * *